United States Patent
Hill et al.

[11] Patent Number: 6,021,845
[45] Date of Patent: Feb. 8, 2000

[54] WIDE TEMPERATURE RANGE HEATING/COOLING INTERFACE WITH RAPID RESPONSE

[76] Inventors: Dennis Hill, 11 Hackney Way, Harleysville, Pa. 19438; Terence Rufer, 281 Landis Store, Boyertown, Pa. 19512; Ravi Bains, 1942 Riverbend Rd., Allentown, Pa. 18103

[21] Appl. No.: 09/052,605

[22] Filed: Mar. 31, 1998

[51] Int. Cl.[7] ........................................... F28F 27/00
[52] U.S. Cl. ............................................. 165/96; 165/185
[58] Field of Search ..................... 165/96, 185; 62/903

[56] References Cited

U.S. PATENT DOCUMENTS

| | | | |
|---|---|---|---|
| 3,229,755 | 1/1966 | Komarow | 165/96 |
| 3,330,333 | 7/1967 | Moss | 165/96 |
| 3,643,734 | 2/1972 | Deschamps | 165/96 |
| 4,112,699 | 9/1978 | Hudson, III et al. | 165/96 |

OTHER PUBLICATIONS

Joe Foreman and Kevin Reed, "Dynamic Mechanical Analyzers: How do They Work?", excerpts from TA Instruments marketing brochure, Technical Publication #TA 229, (4 sheets).

"Features of G.C. Cryo–Trap", excerpts from Scientific Instrument Services, Inc. marketing brochure (4 sheets), (A copy of the Scientific Instrument Services, Inc. brochure is attached thereto, Application Note No. 19.)(11 pages).

*Primary Examiner*—Christopher Atkinson
*Attorney, Agent, or Firm*—Helfgott & Karas

[57] ABSTRACT

A sapphire interface with a closed cycle cryogenic cooler replace liquid nitrogen in cryotraps for gas chromatographs, cryofocusers for gas chromatographs, DMA's and DSC's. Inverse thermal properties of sapphire allow the closed cycle cooler to function at cryogenic temperatures at one end of a sapphire element while temperature of a test element is raised at the other end. Quartz and silicon are alternatives to sapphire. Substantial mass of the sapphire interface is eliminated by making the test element an integral part of the assembly and enables use of a smaller capacity cooling system. Low mass provides rapid temperature changes when switching between heating and cooling. The cooling requirement remains substantially constant, whether a test sample is heated or cooled.

24 Claims, 6 Drawing Sheets

WIDE TEMPERATURE RANGE HEATING/COOLING INTERFACE WITH RAPID RESPONSE

BACKGROUND OF THE INVENTION

Situations have developed in laboratories and in industry, where operations over a wide range of temperatures are mandated, and very rapid changes between extremes of temperature may provide advantages that enhance results and provide economies of operation.

For example, gas chromatographs are used to determine the quantities of chemical components making up a liquid or gas sample, and cryogenic cooling is used for several purposes associated with gas chromatographs. For chromatography, a gas or liquid sample is fed through a cryotrap at cryogenic temperatures to freeze out unwanted contaminants, the most common being water, and the remainder of the sample flows from the trap and into the gas chromatograph for analysis. After the analysis is completed, the temperature of the cryotrap is raised to an elevated temperature, which may be as high as 400° C., to purge the trap of contaminants prior to evaluating another sample. It is advantageous in a series of operations if cool-down and heating times are minimized.

Sometimes, in addition to a cryotrap, a cryofocuser, also referred to as a cryoconcentrator, is used to condense the constituents of interest so that they are concentrated inside the cryofocuser. Then, the temperature of the cryofocuser is raised rapidly to an elevated level to quickly release the accumulated components of interest. This sequence effectively raises the sensitivity of the analysis by concentrating the target components over a longer time period than the time period for delivery to the chromatograph.

Cryofocusers generally operate in a range between –200° C. and 400° C. In both instances, cryogenic cooling is accomplished by evaporation of liquid nitrogen.

A second device called a Dynamic Material Analyzer (DMA) is used to characterize the stiffness and damping of material samples by imposing sinusoidal deflections on one side of the sample and measuring the resultant force transmitted to the other side of the sample. Frequency is often varied to determine the changes in material stiffness and damping that occur with frequency. Many DMA's also have the capability to measure material properties for temperatures ranging from –150° C. to 600° C. Again, cryogenic cooling is currently accomplished by evaporating liquid nitrogen.

Differential Scanning Calorimeters (DSC) determine the heat capacity of materials as a function of temperature by measuring the rate of temperature change of the sample for a known heating rate and sample mass. The temperature range of interest is frequently –100° C. to 750° C., and again, cooling is currently accomplished by use of liquid nitrogen.

Attributes common to the three applications are the need to cool samples to cryogenic temperatures, to perform measurements over a broad range of temperatures, and the need to vary the temperature up or down rapidly. As stated, the current method of cooling in all three applications is the use of liquid nitrogen; on the other hand, sample temperature is increased by powering an electric heater.

In a typical cryotrap function for a gas chromatograph, liquid nitrogen flows into a chamber around an object to be cooled; the object may be a capillary tube. A resistance wire heater is wrapped around the capillary tube. Temperatures between room temperature and the boiling temperature of liquid nitrogen (–196° C.) are attained by a combination of modulating electrical power to the heater and pulsing the flow of liquid nitrogen on and off. Temperatures above room temperature are attained by not flowing liquid nitrogen, and simply powering the heater. It is a crude method of temperature control, especially since continuous modulation of $N_2$ flow using automatic thermo-mechanical devices is not reliable or easily achieved. Liquid carbon dioxide (boiling temperature –78° C.) is also sometimes used as a refrigerant instead of liquid nitrogen.

With such apparatuses, and in other laboratory test equipment involving wide ranges of temperature, it is most desirable that changes in temperature can be effected rapidly. The rapidity of temperature change depends upon the required range of temperature and the mass that is being heated and cooled during operation. Thus, the structure that supports, for example, a test sample in a gas chromatograph, is important as its mass may be greater than the mass of the sample to be tested. In such an application, the cooling and heating requirements are small for the sample and relatively substantial for the apparatus. The total mass should be minimized so that the cool-down time and warm up times are low. Heating and cooling a large mass not only increases the response time but also increases the requirements for liquid refrigerant that is evaporated during the cooling process and that may be used as a modulator during the heating process.

Also, to keep the cooling load low at the cryogenic temperature interface, it is necessary to isolate the heating source from the cooling source as much as possible. When complete isolation is not possible, excessive heat reaches the cooling source while heating a test sample and a larger heat removal capacity than at cryogenic temperatures is required, especially when cooling continues during heating. On the other hand, if cooling is entirely shut down during heating operations, the structure is warmed and the response time is very slow when cooling is again required.

For these reasons, a closed cycle cryocooler system has not been used in chromatograph, DMA and DSC applications. A closed cycle cryocooler that is adequate solely for cooling would be overwhelmed by unwanted heat, conducted through the sample, during heating of the sample. As a result, the cryocooler's cold head temperature would rise; its response time when the sample was to be cooled would be slow.

Using a sapphire to make a thermal interface for cryogenic refrigerators is not a novel concept. The assignee of the present application has been using sapphire interfaces since 1983, and manufactures and offers for sale sapphire interfaces for laboratory experiments. Others also sell a sapphire interface.

Sapphire has unusual, but well known properties, namely a high thermal conductivity at cryogenic temperature and a low thermal conductivity at elevated temperature. The thermal conductivity of sapphire versus temperatures is compared with that of stainless steel and copper in FIGS. 1a,b.

In use as an interface, the object to be temperature-controlled is placed at one end of a sapphire rod together with a heater. The cold tip (cold head) of a commercially available closed cycle cooler is placed at the opposite end of the sapphire rod. When the temperature of the object is raised by the heater, the temperatures at the heater-end of the sapphire and of the entire assembly are also somewhat elevated. Warming the sapphire lowers its thermal conductivity, and the amount of heat which reaches the closed cycle cooler by conduction through the sapphire is thereby not linearly related to the increasing temperature difference between the ends of the sapphire. Since the thermal conductivity of sapphire decreases rapidly with temperature increase, the sapphire effectively acts as a control that limits the amount of heat transferred to the closed cycle cooler. Therefore, a smaller refrigeration cycle can operate without overloading or wide swings in its cold temperature during warming of the test object, than would be feasible without the intermediate sapphire interface.

As is known, the amount of heat which the sapphire element (or any solid rod) will conduct from one end to the other is related directly to the thermal conductivity of the element, cross sectional area of the element, element length, and the temperature difference from one end of the element to the other end (length). The amount of heat transferred is inversely related to the length of the element.

Thus, in determining the quantity of heat that will flow through the sapphire rod, thermal conductivity is a variable dependent upon temperature, and temperature is a variable. Length and cross sectional area are fixed by design. The amount of heat that will be transferrable by the sapphire rod at any given conditions is therefore determined by the product (integral) of thermal conductivity (at that time) and temperature differential across the element (at that time).

FIG. 2 displays the mathematical product of thermal conductivity and differential temperature $\Delta T$ for four materials of interest, individually normalized by dividing by the maximum value of the product for each material respectively over the temperature range of interest. In FIG. 2, it is assumed that the cold temperature $T_c$, for example, at one end of the sapphire, remains constant at 80K. The "heat station" is the opposite end of the element where the heater would typically be mounted and in heating a maximum temperature $T_h$ of 800K. is reached. The sapphire displays a desirable property of the product of thermal conductivity and differential temperature, which product is substantially constant over a major portion of the entire temperature range. This characteristic is in contrast to the heat transfer rate (product) of copper and stainless steel, which materials show poor heat transfer at the low temperatures and high heat transfer at high temperatures. A second material, quartz, which is usable in place of sapphire, also has a relatively constant heat transfer rate. Materials showing an upward arc in a graph such as FIG. 2 are generally usable with advantage in a thermal interface. Presently known, sapphire has the highest performance potential. Quartz is acceptable in many applications. Materials having $k\Delta T$ properties between quartz and sapphire, such as single crystal silicon, are good alternatives to sapphire. Other suitable materials including ones superior to sapphire, may be developed in the future and are considered to fall within the scope of the present invention.

With regard to FIG. 2, which is a normalized graph of the thermal conductivity integral versus temperature, it is easy to identify which materials provide an advantage in a thermal interface in accordance with the invention. It is apparent, whether or not the thermal conductivity changes in a manner that reduces the load at the system cold head when the test subject is being heated, and the cooling system is simultaneously operated.

A material having a thermal conductivity that is independent of temperature changes, would plot on such a graph as a straight line between the selected temperatures of $T_c$ 80K. and $T_h$ 800K. The slope of that line would be $1/(T_h-T_c)$. Any material that graphically "bulges" upward from that line, such as quartz and sapphire in FIG. 2, would be favorable for the thermal interface in accordance with the invention and would be characterized by a slope at $T_c$ (80K.) greater than the slope $1/(T_h-T_c)$. Also, the slope of the "bulging" line at $T_h$ (800K.) would be less than the slope $1/(T_h-T_c)$. Materials having a characteristic that on a graph similar to FIG. 2 falls below a straight line connecting $T_c$ and $T_h$, would be unfavorable for use in the present invention. The load on the cold head would increase unfavorably when the test subject was heated and would require a larger cooling system if successful operations are to be achieved as compared to the upper-bulging type materials.

It should be understood, that a graph similar to FIG. 2 can also be provided without normalizing the values of the ordinate. This will result in a wide range of values plotted for the ordinate, whereas, when normalized, the ordinate always has a range from 0–1. Normalizing makes for easier comparison of materials. It can be readily seen in FIG. 2 that when cooling from 800° to 80° K., the sapphire will provide the greatest capacity for cooling and therefore the quickest cooldown.

Nevertheless, the known sapphire interface only partially resolves the problems associated with heating and cooling of a sample over a wide range in that the commercially available interfaces have high mass and therefore relatively low response time. As a result a sapphire interface and closed cycle refrigerator have not been applied in gas chromatographs, DMAs and DSCs.

It is generally desirable in these applications to heat up and cool-down from temperature extremes in a matter of minutes, whereas, cool-down time for commercially available closed cycle coolers ranges from 15 minutes to hours. Thus, to be useful in these special apparatuses, a closed cycle cooler must remain cold while the heat station with the test object or sample is warmed in order to subsequently achieve rapid cooling at the heat station.

The amount of heat which is allowed to flow into the cooler while a test object is heated must be limited to prevent the cooler from warming up. With conventional materials like copper and stainless steel, maximum heat transfer takes place when the heat station is at maximum temperature, as shown in FIG. 2, and the heat transfer rate drops off rapidly from that point. For sapphire, the heat transfer rate is close to maximum across the whole temperature range of interest. The higher the heat transfer rate during cool-down, the faster the cool-down. Since the heat transfer rate for sapphire remains close to maximum throughout the temperature range, a sapphire interface can provide the most rapid cooling rate.

What is needed, is a heating/cooling wide temperature range interface that eliminates the need for expendable liquid refrigerant, provides rapid response times and satisfies these conditions with low maximum cooling requirements.

SUMMARY OF THE INVENTION

This invention makes use of a sapphire interface with a closed cycle cryogenic cooler to replace the use of liquid nitrogen in cryotraps for gas chromatographs, cryofocusers for gas chromatographs, DMA's and DSC's. The use of sapphire stems from its desirable thermal properties, allowing the closed cycle cooler to function at cryogenic temperatures at one end of the sapphire element while the temperature of the test article is raised at the other end of the sapphire element. Quartz (fused silica) may be used as an alternative to sapphire, but has less optimal thermal properties. Single crystal silicon has conductivity/temperature characteristics that fall between those of sapphire and quartz. Thus, this material is another known alternative for use in an interface in accordance with the invention.

Additionally, substantial mass that was present in prior art sapphire interfaces is eliminated in the present invention by making the test element an integral part of the interface assembly. Thus, the sapphire better isolates the closed cycle refrigerant cryogenic cooler from the heater and enables use of a small capacity cooling system. At the same time, low mass allows for rapid temperature changes when switching between heating and cooling at different locations within a wide, available temperature range. The cooling requirement, whether a sample is heated or cooled, remains substantially constant whereby the cryogenic cooler cycle is sized without excessive capacity. The advantages of a closed cycle refrigerator over an open cycle that evaporates refrigerant, are achieved.

Further, objects and advantages of the invention will be apparent in the specification and drawings. The invention accordingly comprises the features of construction, combination of elements, and arrangement of parts, which will be exemplified in the constructions hereinafter set forth, and the scope of the invention will be indicated in the claims.

BRIEF DESCRIPTION OF THE DRAWINGS

For a fuller understanding of the invention, reference is had to the following description taken in connection with the accompanying drawings, in which.

DESCRIPTION OF PREFERRED EMBODIMENTS

Before describing interfaces in accordance with the invention, a description is presented of a prior art interface, manufactured by the assignee of the present application, to illustrate problems associated with construction of an effective device.

Figure 3:
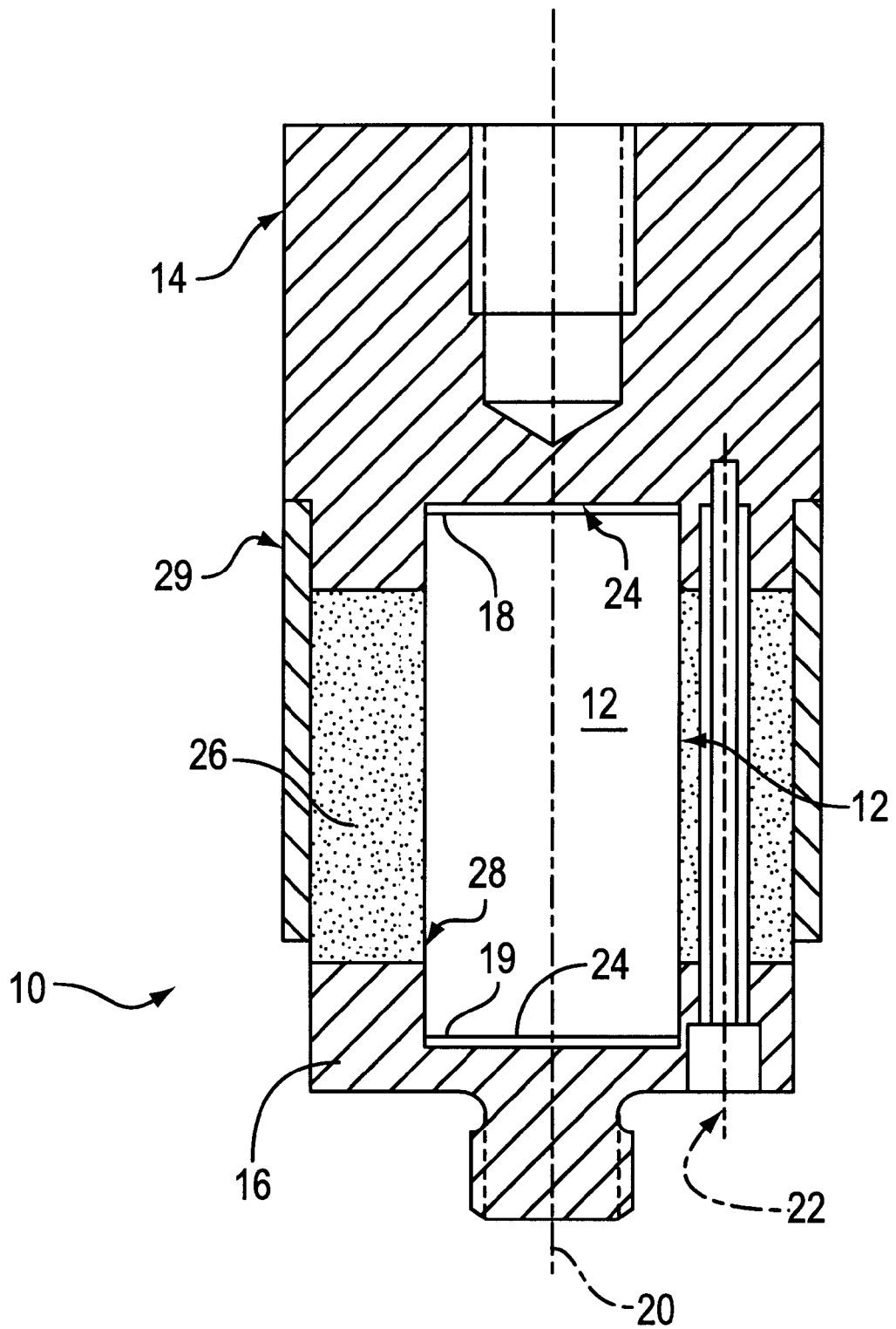
FIG. 3 is a thermal interface unit of the prior art.

With reference to FIG. 3, an interface 10 includes a sapphire rod 12 supported between a top end piece 14 and a bottom end piece 16 made of a high thermal conductivity material, for example, copper. The sapphire rod 12, a circular cylinder, is seated in recesses 18, 19 of the end pieces 14, 16 to assure concentric positioning relative to a center line 20.

Three equi-spaced screws 22 (one shown) connect the top end piece 14 to the bottom end piece 16, and when tightened place the sapphire rod 12 in compression. Sapphire has a high compressive strength and is not damaged. Thin gaskets 24 of highly conductive material, for example silver, are positioned between the axial ends of the sapphire rod 12 and the end pieces 14, 16. The gaskets reduce the thermal contact resistance between the end pieces 14, 16 and the sapphire rod 12 as the soft silver when compressed squeezes into surface imperfections and accounts for slight misalignments at the joints. The net result is better heat transfer between the copper and sapphire by way of the gaskets 24.

An insulating jacket 26, for example, epoxy, surrounds the sapphire rod 12 where the rod is not enclosed by the end pieces 14, 16, and is bonded to the lateral cylindrical surface 28 of the sapphire rod 12. The jacket 26 provides torsional rigidity for the interface 10 but may limit the operational temperature of the interface. With an epoxy jacket, the upper temperature limit is approximately 200° C.

For operational temperatures less than room temperature, the screws 22, which are usually steel, contract more than the sapphire rod 12, putting the sapphire acceptably in compression. For operation above room temperature, the steel screws 22 expand more than the sapphire rod 12, tending to relieve any preload on the screws. Further expansion causes these screws 22 to be loosely fitted with the bottom end piece 16, whereby the interface 10 is held together by the bonding between the jacket 26, the sapphire rod 12, and the end pieces 14, 16.

When the jacket 26 is epoxy and operation is at levels above room temperature, the epoxy jacket 26 expands more than the sapphire rod 12, tending to place the sapphire in tension. However, because the epoxy is much softer than the sapphire rod, the tensile load on the sapphire rod 12 is small and within acceptable limits.

A copper sleeve 29 surrounds the jacket 26 to provide rigidity such that the sapphire rod 12 is well protected from external shocks, vibrations, twisting, etc. which are dangerous to the fragile sapphire material. The copper sleeve 29 is connected to the top end piece 14 and to the jacket 26 but does not extend to or contact the lower end piece 16. Thereby, a possible path for heat leakage from one end to the other end of the interface 10 is substantially eliminated.

It should be noted that there are three major thermal paths between the top end piece 14 and the bottom end piece 16, namely, the sapphire rod 12 with its variable conductance, the steel screws 22, and the insulating jacket 26.

In use, the interface 10 has one of the ends 14, 16 connected to a source of cryogenic cooling, for example, a closed cycle cryocooler unit. The other end is generally connected to the object being evaluated where heating is provided so that the temperature of the test object can be raised or lowered by application of electrical energy.

Figure 1A:
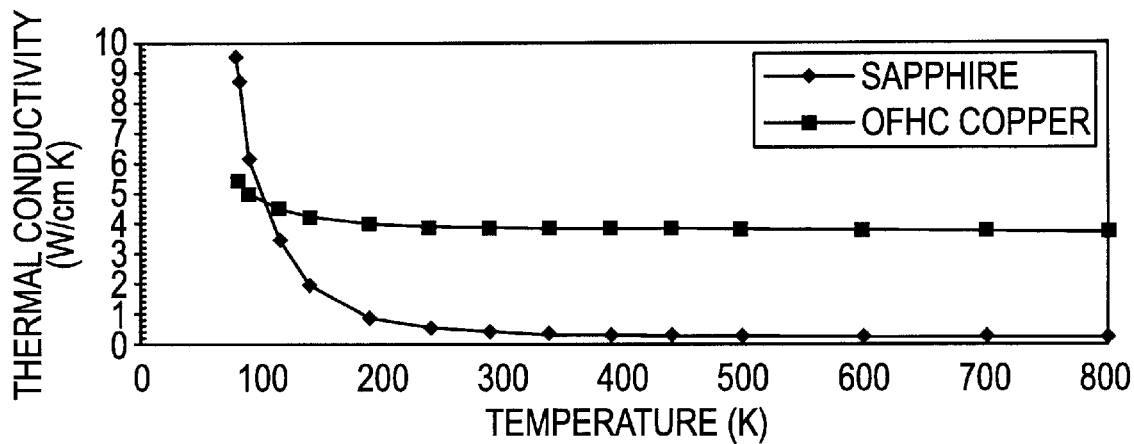
FIGS. 1a and 1b are thermal conductivity characteristics of materials used in thermal interfaces units in accordance with the invention.

Because the conductivity of the sapphire rod 12 changes so dramatically (FIG. 1a) the rod 12 presents a low resistance path, high conductivity, for the transfer of heat at cryogenic temperatures that are provided by the cryocooler. On the other hand, when the temperature at the heated end of the sapphire rod 12 is elevated, the sapphire presents higher resistance, lower thermal conductivity, for heat flow from the heated side of the interface 10 to the side being cooled continuously by the cryocooler. The flow of heat from the hot side of the sapphire rod 12 to the cold side is regulated by the sapphire such that the cryocooler is not overloaded, nor is its cold temperature substantially changed, when the test object is heated.

When the test object is to be cooled below room ambient, the electrical heater may be turned entirely off or its input may be modulated to meet particular temperature conditions. The full range of operation is maintained within the capability of the cryocooler, which, as stated, may operate continuously. Thus, long periods conventionally required to bring a cryocooler to stable operation from a start up may be eliminated after testing conditions have once been achieved.

Figure 4A:
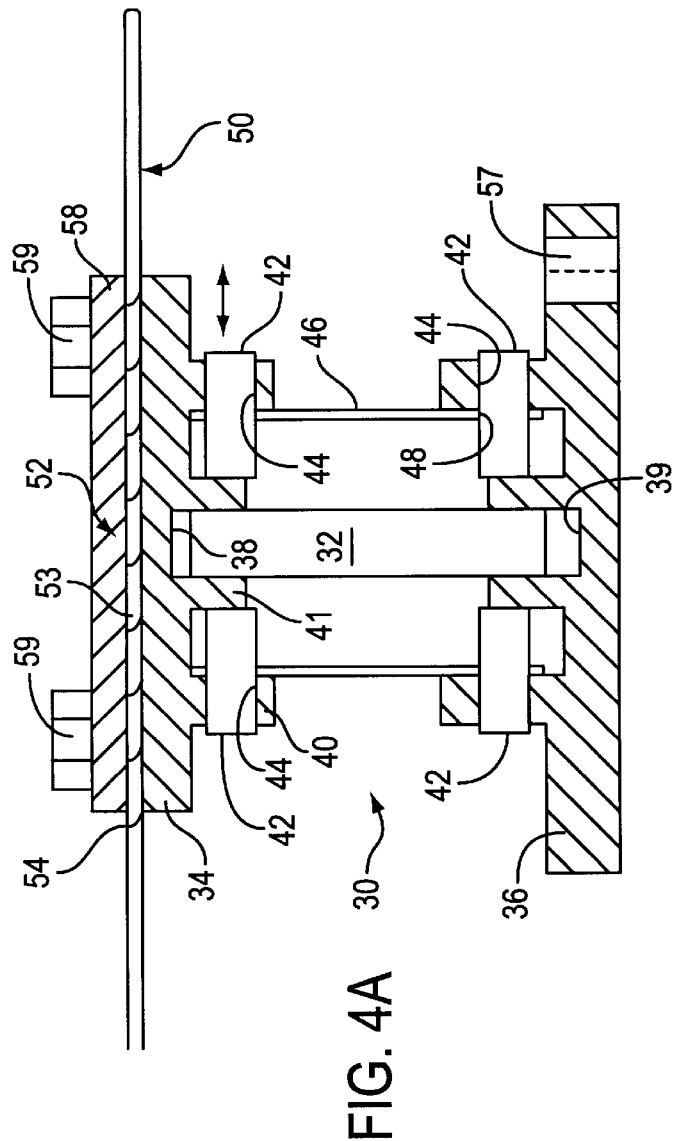
FIGS. 4a and 4b are respectively an elevational view in section and top view of an embodiment of an interface unit in accordance with the invention.

With reference to FIGS. 4a,b, an interface 30 in accordance with the invention, for use in a gas chromatograph, includes a sapphire rod 32 extending between a top end piece 34 and a bottom end piece 36 and into respective recesses 38, 39 therein.

The end piece 34 is a plate from which two annular walls 40, 41 extend toward the bottom end piece 36. The inner wall 41 defines the lateral surface of the recess 38. Set screws 42 on opposite sides of the sapphire rod 32 pass through threaded openings 44 in the outer wall 40 and press on the inner wall 41 at opposed locations. Thus, by tightening the set screws 42, the inner wall 41 is deflected to press laterally on the longitudinal end of the sapphire rod 32 where the rod is seated in the recess 38.

A similar construction is provided at the bottom end piece 36 to laterally compress the sapphire rod 32 at the longitudinal end that is recessed in the lower end piece 36.

A protective tube 46 surrounds the sapphire rod 32 and extends between the top end piece 34 and the bottom end piece 36. The screws 42 thread through tight fitting holes 48 in the tube 46. The tube 46 provides axial, bending, and torsional rigidity, and protects the fragile sapphire rod 32 during installation and handling of the equipment. Both the physical and thermal characteristic of the tube 46 are important considerations in that the tube 46 represents a heat flow path for leakage between the top and bottom end pieces 34,36, and also exerts physical forces on the sapphire rod 32 during changes in temperature.

Titanium, for example, the Ti-6Al-4V alloy, has been found effective for the tube 46 in prototype units. Titanium has very low thermal expansion for a metal. When the interface 30 operates below room temperature, the titanium tube 46 contracts more than the sapphire rod 32, putting the sapphire into compression. On the other hand, when the interface 30 is operating above room temperature, the titanium tube 46 expands more than the sapphire rod 32, putting the sapphire material into tension. The tensile stress in the sapphire increases with increased temperature and would reach a failure point at approximately 1050° C. However, this temperature is above the normal operating range for the interface 30 when the end pieces 34, 36 are made of copper. Thus, the tension induced by expansion of the titanium tube 46 is not the limiting factor in performance of the interface 30.

Figure 1B:
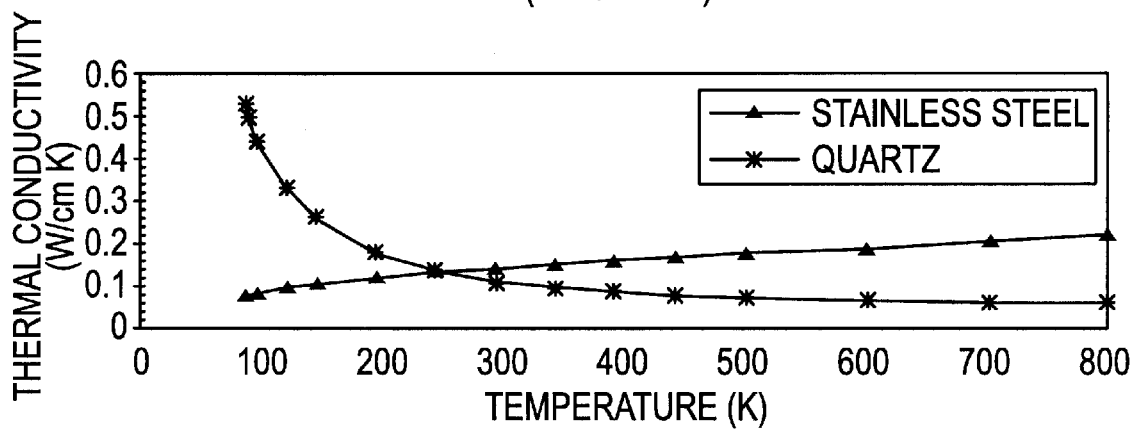
Figure 2:
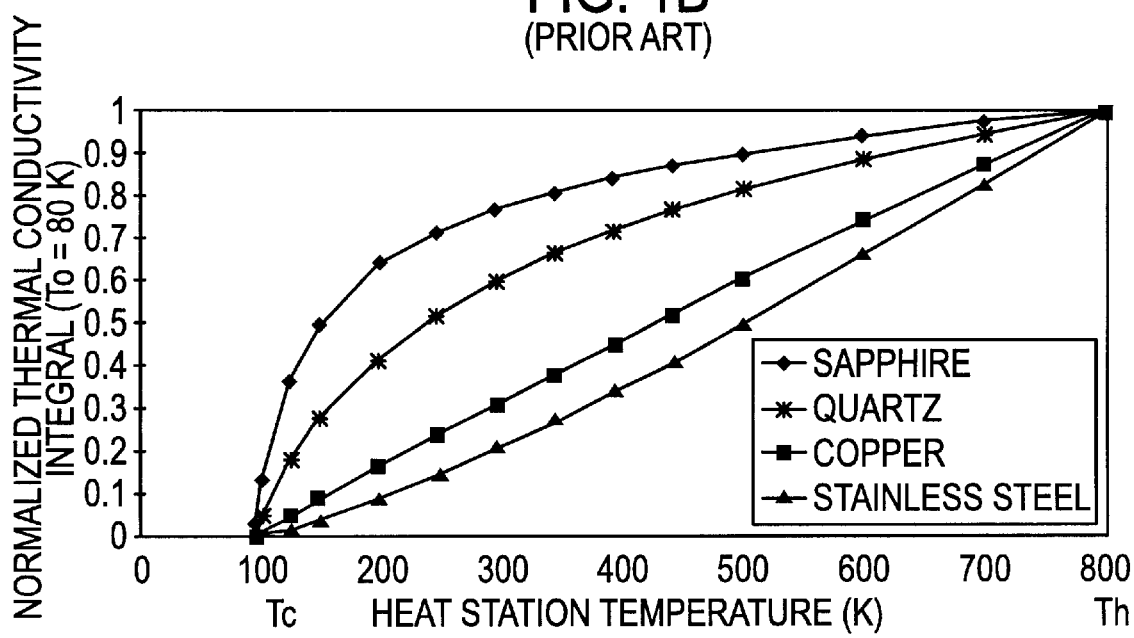
FIG. 2 illustrates relative heat transfer characteristics of the materials in FIGS. 1a, b versus temperature.

Another advantage of titanium is its very low thermal conductivity, which is less than that of stainless steel, although it increases with temperature in a manner similar to that of the thermal conductivity of stainless steel (FIG. 1b). Ideally, the outer protective support tube 46 would transfer no heat; then only the sapphire rod 32 with its advantageous thermal conductivity properties would transfer heat. In actuality, some heat from the upper end piece 34, generally made of copper, is transferred down the titanium tube 46 to the lower end piece (copper) 36, which is attached to a closed cycle cryogenic cooler (not shown). Less, but still undesirable heat transfer occurs with the titanium tube 46 than with the steel screws 22 in the prior art embodiment of FIG. 3.

A quartz tube 50 passes through a V-notch groove 52 in the top surface 53 of the top piece 34, and is wrapped with a heater wire 54, for example, nickel-chromium, so that the tube 50 itself and its contents may be heated by application of electrical energy to the wire. The nickel chromium wire is insulated with a thin layer of ceramic paste (not shown) before being clamped into the assembly.

The quartz tube 50 is secured by the plate 58, which is clamped to the top end piece 34 by bolts 59. Bolt holes 57 are provided in the bottom end piece 36 for use in attachment to the cold head (not shown) of a cryocooler.

Sample gases flowing to a gas chromatograph (not shown) may pass through the quartz tube 50 either directly or within another tube, for example, a capillary tube that contains the sample gas. While passing through the interface 30, the sample gas may be heated and cooled in any desired sequence when the bottom end piece 36 is connected to a continuously operating cryocooler.

Under conditions of heating, the major portion of the heat load that passes from the hot side to the cold side through the sapphire rod 32 and titanium tube 46, is carried by the sapphire rod. For example, at 800K. (527C.) the effective thermal conductivity (integral) of the sapphire rod 32 is eight times that of titanium.

Silver gaskets (not shown) may be used between the sapphire rod 32 and the top and bottom end pieces 34, 36 with compressive contact between them to enhance the heat transfer capabilities, as discussed with reference to the prior art gaskets 24. In FIGS. 4a, b, such gaskets may be hollow cylindrical sleeves that surround those lateral portions of the sapphire rod 32 that are within the recesses 38, 39.

When using a silver gasket between copper end pieces 34, 36, the interface 30 would be limited to operation at temperatures not exceeding 950° C. because of the gaskets. In the absence of a silver gasket, the maximum operating temperature is limited to 1,000° C. by the copper pieces 34, 36.

In a construction demonstrating satisfactory performance, the sapphire rod 32 was 0.125 inches in diameter by 0.625 inches long. The tube 46 was of titanium alloy, as indicated above, having a diameter of 0.5 inches and a wall thickness of 0.022 inches. Such a sapphire rod 32 had a maximum capability of transferring 30 watts of energy when a temperature of 300° C. was provided (573K.) by a 100 watt controlled heater wire 54 and a cryocooler provided a cold end temperature of –193C. (80K.). Basically, the dimensions of the sapphire rod 32 determine the heat transfer rate during cooling. Sapphire rods are available from Insaco, Inc. Quakertown, Pa.

Based upon a predetermined heat transfer rate, the design can be optimized. That is, the interrelationships between heat transfer rate, desired cool-down time and maximum thermal mass of the interface can be traded off in accordance with the particular application of the interface. The mass at the end of the interface, where the test object or sample will be located and where cyclic temperatures are desired, should be minimized so that cool-down time and warm-up time are low.

The temperature cycle of the refrigerator is relatively unimportant as long as the cooling system is sized with the maximum thermal capacity of the closed cycle cooler matching the maximum heat transfer rate (when the test object or sample is at elevated temperature) of the thermal interface at the elevated steady state operating temperature. Then, the interface can be held at its maximum design heating temperature indefinitely without exceeding the capacity of the cryocooler or substantially changing its cold head temperature.

Figure 5A:
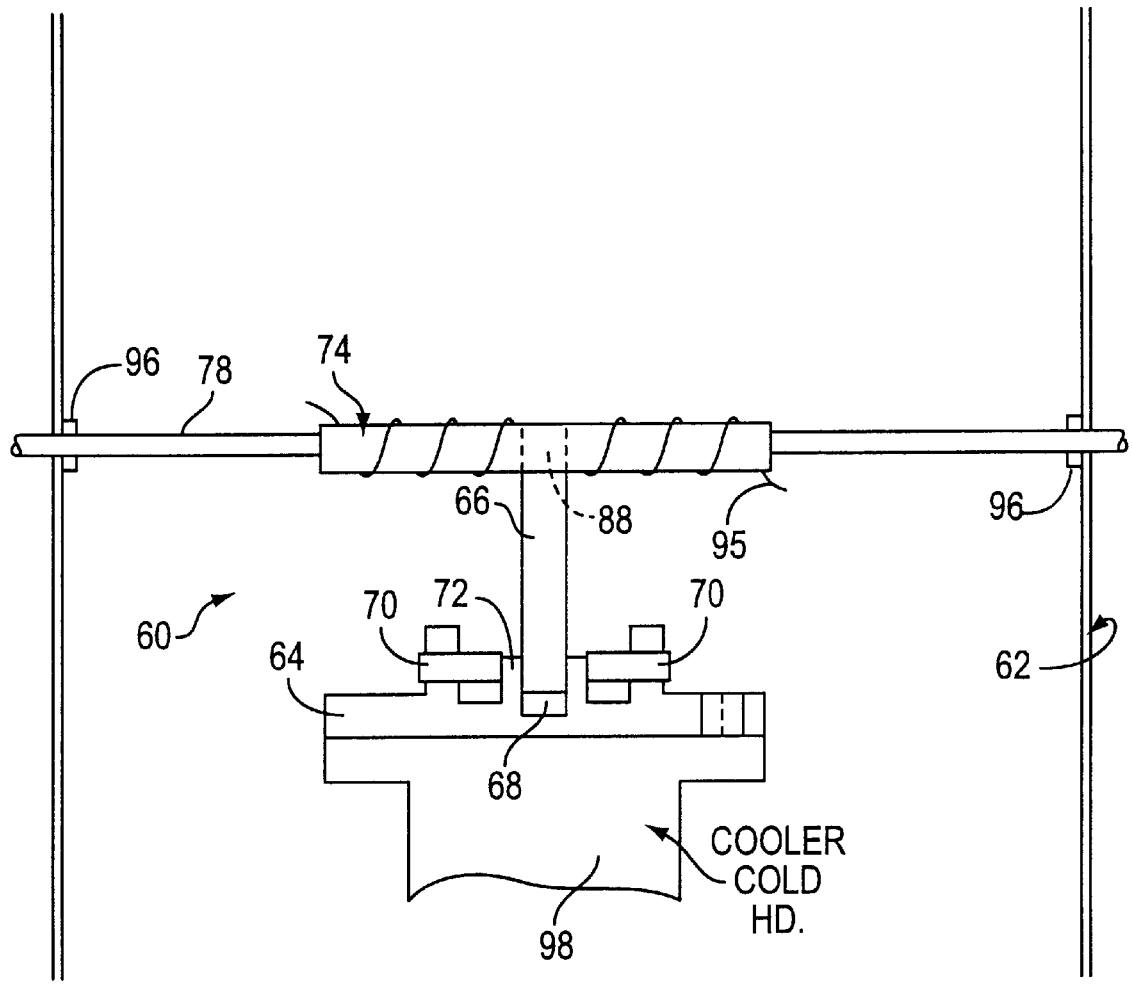
FIGS. 5a and 5b are respectively a partial elevation and top view of an alternative embodiment of an interface unit in accordance with the invention.
Figure 5B:
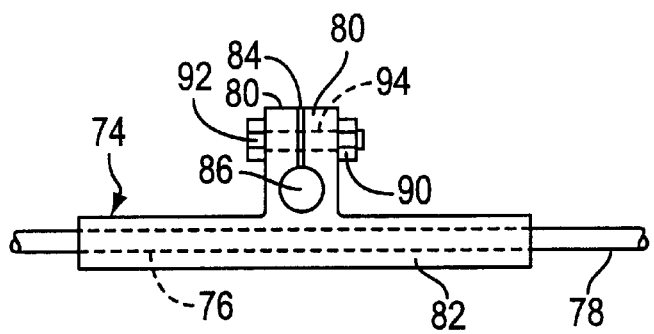

Another alternative embodiment of an interface 60 in accordance with the invention is illustrated in FIGS. 5a and 5b. Interface 60 is a low mass construction of an interface operating within a vacuum housing 62, for example, stainless steel, as part of a gas chromatograph system.

A bottom end piece 64, which is similar to the bottom end piece 36, supports a sapphire rod 66 in a recess 68. A pair of opposed set screws 70 act on the inner wall 72 to hold the sapphire rod 66 in position under lateral compressive force, as in FIG. 4a.

The upper end piece 74 is basically a cylinder of highly thermally conductive material, for example, copper, having a central axially extended opening 76 through which a tube 78 of relatively low thermal conductivity material (e.g. stainless steel) passes.

A pair of tabs 80 extend transversely from the cylindrical portion 82 of the upper end piece 74, and a small slot 84 separates the tabs 80. A circular opening or socket 86 passes through the base of the tabs 80 and receives therein the upper end 88 of the sapphire rod 66.

By tightening a nut 90 on a bolt 92 that extends through a clearance hole 94 in the tabs 80, the tabs 80 exert lateral compressive forces on the cylindrical surface of the sapphire rod 66. Thus, the forces on the sapphire rod 66 are substantially the same as those which are provided in the embodiment of FIG. 4a.

A heater wire 95 encircles the cylindrical portion 82 of the upper end piece 74 to provide heating when required. The stainless steel tubing 78 is supported in the walls of the vacuum housing 62. Vacuum sealed connections 96, well known in the art, (e.g. manufactured by Swagelok Company, Solon, Ohio) are used to grip the tubing 78 and preserve the vacuum within the housing 62.

As constructed, the tube 78 becomes the support at one end for the sapphire rod 66 and the throttle cycle cooler 98 supports the other end of the sapphire rod 66 by virtue of the cooler's support (not shown) within the vacuum housing 62.

The gas sample to be evaluated in a chromatograph is passed through the tubing 78, (for example 1/16th inch stainless steel) and is subjected to heating and cooling at the interface 60. A good thermal bond is provided between the tube 78 and the end piece 74. Alternatively, a smaller diameter quartz tube (not shown) may be passed through the tube 78, and the gas sample passed through the smaller quartz tube.

Figure 4B:
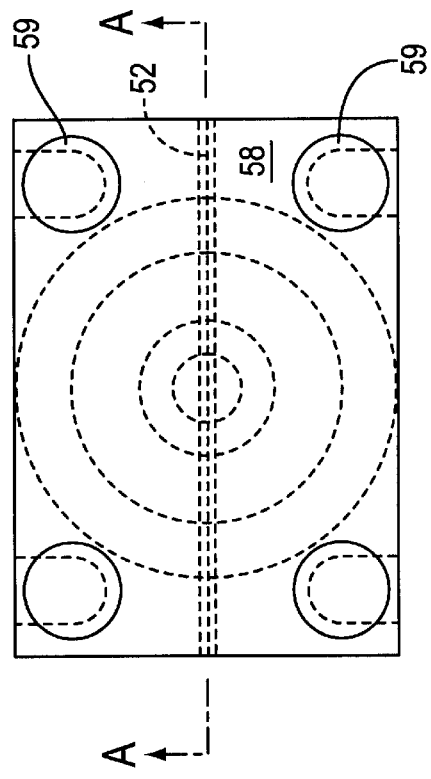

An interface in the configuration of FIG. 4 had a temperature cycled mass of 40.3 grams, and interface 60 of the construction in FIG. 5A weighed only 5 grams and was cooled from 400C. to −190C. in approximately two minutes. The heavier interface (FIG. 4) would require approximately 16 minutes for cooling the same load though the same temperature range, and the prior art device of FIG. 3, having greater mass would require an even longer time period. When used as a cryofocuser, an interface 60 in accordance with the invention could be cycled rapidly from −200C. to 500C. and back to −200C. without exceeding the capacity of the throttle cycle cooler and without intermediate adjustment to the cooler's performance.

The interfaces 30, 60 in accordance with the invention can be used in applications where closed cycle cryogenic refrigerators have never been used and eliminate the need and inconveniences associated with use of liquid refrigerants such as nitrogen and carbon dioxide.

However, use of the low mass interfaces in accordance with the invention is not limited to applications having closed cycle refrigerant systems, but also may be used with evaporating liquid refrigerants such as liquid nitrogen and carbon dioxide at the cold end. In such applications, the need to adjust a flow rate of liquid refrigerant may be eliminated. Substantially less refrigerant would be expended, and lower mass interfaces would achieve shorter response times.

Figure 6:
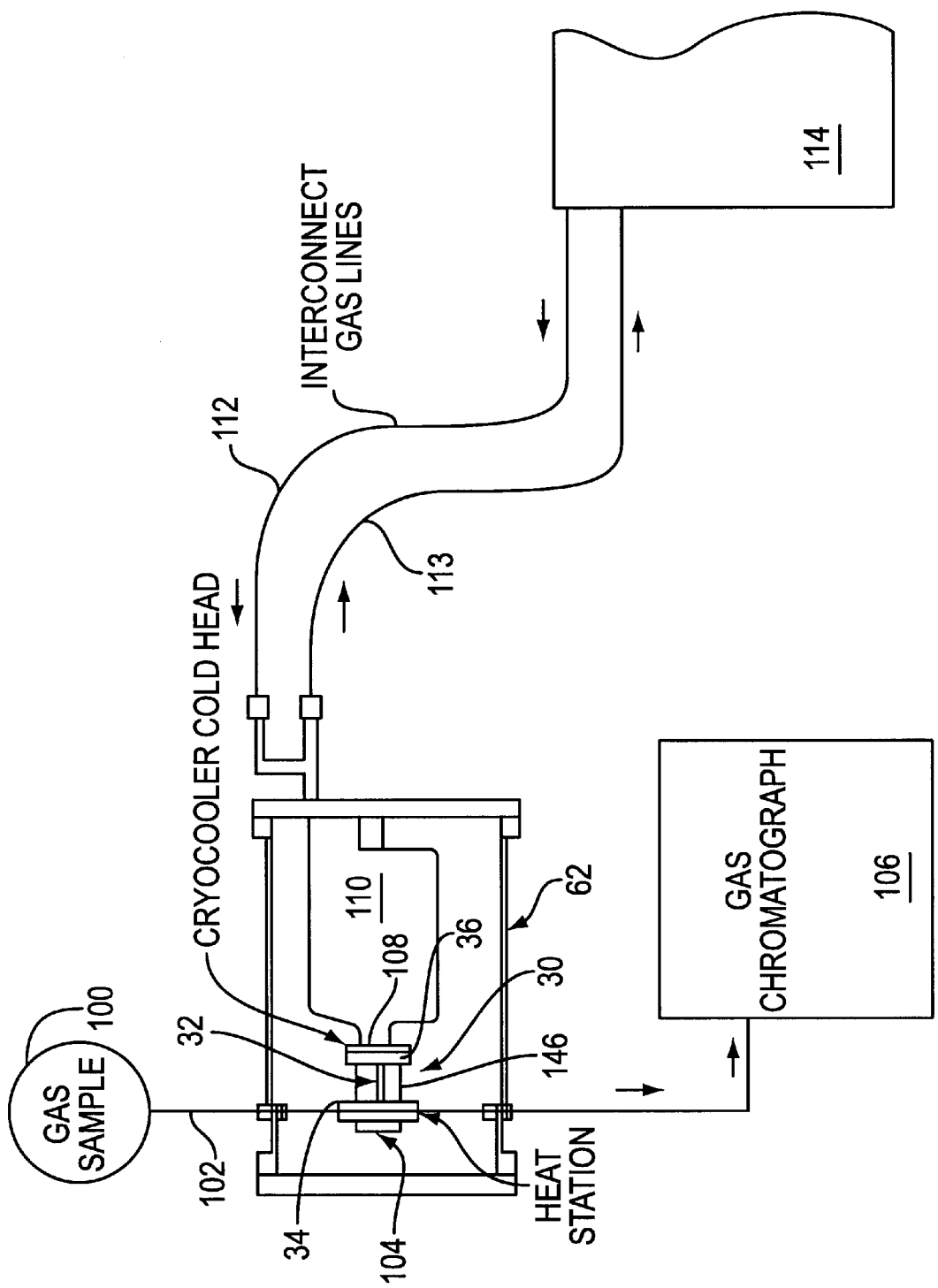
FIG. 6 is a gas chromatograph system using an interface in accordance with the invention.

FIG. 6 is a schematic representation of a gas chromatograph system using an interface 30 in accordance with the invention in conjunction with a cryocooler closed cycle refrigeration system. Heating and cooling are carried out within the vacuum chamber 62 and the cold portions of the cryosystem are also within the vacuum canister so as to minimize unwanted heat loads from the ambient environment. Thereby, system performance is optimized.

In the gas chromatograph system, a gas sample flows from a sample container 100 through a tubing 102 to the interface 30 where the gas may be heated and/or cooled as discussed above in proper timed sequences by heater 104. When leaving the interface 30 the gas flows to the gas chromatograph 106 for analysis. The bottom piece 36 of the interface 30 connects to the cold head 108 of the cryocooler system. Cold portions 110 of the cryocooler system are also within the vacuum chamber 62. Interconnecting gas lines 112, 113 carry refrigerant to and from the cold portions 110 and are near room ambient temperature or at elevated temperatures relative to the ambient. These lines 112, 113, connect to a cryocooler compressor 114. The cryocooler system including the cold head and compressor and all intermediate elements and controls are not novel in themselves and accordingly are not described in detail herein. In FIG. 6, the sapphire rod 32 is protected by a titanium sleeve 46.

Figure 7:
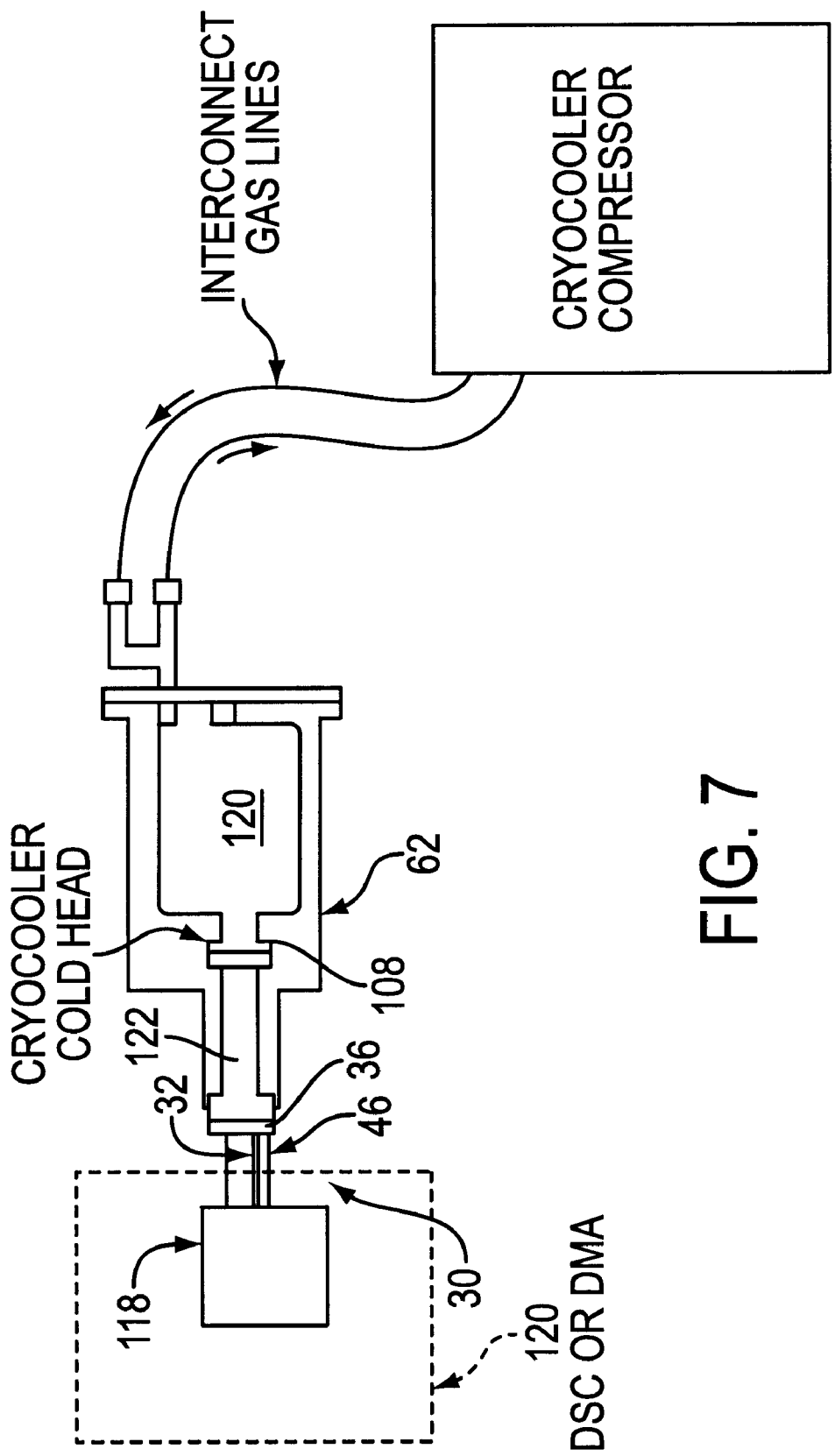
FIG. 7 is a DSC or DMA system using an interface in accordance with the invention.

FIG. 7 shows the interface 30 in accordance with the invention used for a DSC or DMA application. In this embodiment, portions of the refrigeration closed cycle system are within the vacuum housing 62, but the test article 118 is not in a vacuum nor is the heating end of the interface 30.

The test article 118 is located within the DSC or DMA 120 where the heater (not shown in FIG. 7) is located. The sapphire rod 32 and titanium tubing 46 extend from the DSC/DMA and the bottom piece 36 connects to a highly conductive (copper) thermal bus bar 122 that serves as a conduit between the sapphire rod 32 and the cold head 108 of the cryocooler system. As in FIG. 6, the cold portions 120 of the closed cycle refrigeration system are within the vacuum housing 62, as is the bus bar 122, to reduce unwanted heat gain from the ambient environment. The compressor and interconnecting lines are external to the vacuum housing 62.

The embodiments illustrated in FIGS. 4a, 6 and 7 include the titanium tube 46 to provide protection for the sapphire rod 32. With proper structural support (not shown) in the system for the hot and cold end pieces 34, 36 of the interface 30 in FIG. 4a, b, the titanium tube 46 may be eliminated, thus reducing the thermal load on the refrigeration cycle.

In alternative variations, in accordance with the invention, of the systems of FIGS. 6 and 7, the vacuum housing 62 may be replaced by a superior thermal insulation that surrounds the cold parts that in FIGS. 6 and 7 are enclosed in the vacuum housing 62. Insulating materials such as silica aerogel or an insulating gas such as Xenon or krypton may be used to reduce the heat load from the ambient environment instead of a vacuum.

It will thus be seen that the objects set forth above and those made apparent from the preceding description, are efficiently obtained, and since certain changes may be made in the above constructions without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which might be said to fall therebetween.

What is claimed is:

1. A heating/cooling interface for operating in a wide temperature range including cryogenic temperatures, comprising:

a variable conductance element having a thermal conductivity that varies inversely with a change in temperature, and a first end and a second end, said ends being spaced apart along a longitudinal axis;

a first thermal interface element contacting said conductance element at said first end for heat transfer between said conductance element and said first thermal interface element, and for connecting to a cold head of a cryocooler system for heat transfer;

a second thermal interface element contacting said conductance element at said second end for heat transfer between said conductance element and said second thermal interface element, and for thermal connection to a sample delivery tube of a gas chromatograph;

means for applying thermal energy to said second thermal interface element;

said sample delivery tube being subject to controllable heating and cooling when said interface is connected to said cold head and said means for applying thermal energy operates, wherein said thermal interface elements apply pressure respectively on a surface of said conductance element to improve thermal conduction between said conductance element and said thermal interface elements, said pressure acting transversely to said longitudinal axis.

2. A heating/cooling interface as in claim 1, further comprising means for applying said transverse pressure.

3. A heating/cooling interface as in claim 2, wherein said ends of said conductance element are received in respective sockets in said thermal interface elements, and said means for applying said transverse pressure includes respective screws on each said thermal interface element, each said screw being threadably engaged with an associated thermal interface element and extending transversely to said longitudinal axis, an end of each said screw engaging an outer surface of the associated socket, rotating said screw in a first direction urging a lateral wall of said socket against said conductance element to restrain said conductance element, rotating said screw in a second direction opposite to said first direction loosening said conductance element in said socket.

4. A heating/cooling interface as in claim 3, wherein the quantity of said screws in each said thermal interface element is at least two, compressive forces applied to said conductance element by turning said screws in said first direction being at least partially in opposition to each other.

5. A heating/cooling interface as in claim 2, further comprising a thermally low conductivity spacer extending between said first and second thermal interface elements and at least partially surrounding said conductance element to isolate said conductance element from unwanted physical contacts and forces.

6. A heating/cooling interface as in claim 5, wherein said spacer is a hollow cylinder of metal.

7. A heating/cooling interface as in claim 6, wherein said metal is one of titanium and a titanium alloy.

8. A heating/cooling interface as in claim 5, wherein a thermal conductance of said spacer is less than a thermal conductance of said conductance element.

9. A heating/cooling interface as in claim 5, wherein said conductance element ends are received in respective sockets in said thermal interface elements, and said means for applying said transverse pressure includes respective screws on each said thermal interface element, each said screw being threadably engaged with an associated thermal interface element and extending transversely to said longitudinal axis, an end of each said screw engaging an outer surface of the associated socket, rotating said screw in a first direction urging a lateral wall of said socket against said conductance element to restrain said conductance element, rotating said screw in a second direction opposite to said first direction loosening said conductance element in said socket, wherein said screws pass through openings in said spacer with a close fit.

10. A heating/cooling interface as in claim 1 wherein said conductive element is one of sapphire, quartz, and silicon.

11. A heating/cooling interface as in claim 1, wherein said second thermal interface element is a tubing having a heater connected thereto.

12. A heating/cooling interface as in claim 11, wherein said interface is within a thermally insulating test chamber and said delivery tube is attached to said chamber for support.

13. A heating/cooling interface as in claim 11, wherein said conductive tubing is oriented transversely to said longitudinal axis of said conductance element.

14. A heating/cooling interface as in claim 11, wherein said sample delivery tube passes through said tubing and is in heat transfer relationship thereto.

15. A heating/cooling interface as in claim 1, further comprising a closed cycle cryocooler system with a cold head, said cold head being connected to said first thermal interface element.

16. A heating/cooling interface as in claim 11, wherein said heater includes a resistance wire circumferentially around said tubing.

17. A heating/cooling interface as in claim 12, wherein said test chamber is evacuated when used to provide insulating properties.

18. A heating/cooling interface as in claim 1, wherein said conductance element ends are received in respective sockets in said thermal interface elements, and further comprising a thin cylindrical gasket of soft high thermal conductivity material in each said socket and positioned between said thermal interface element and said conductance element cylindrical surface.

19. A heating/cooling interface as in claim 18, wherein said gasket material is one of silver and a silver alloy.

20. A heating/cooling interface as in claim 10, wherein a coefficient of thermal expansion of said sapphire is less than a coefficient of thermal expansion of said thermal interface elements, said conductance element being further compressed by contraction of said thermal interface elements relative to contraction of said conductance element when said interface is being cooled to cryogenic temperatures.

21. A test instrument including an evaluation unit for evaluating a test sample for preselected parameters within a wide range of temperatures, comprising:

an interface unit having a high temperature interface and a low temperature interface spaced apart on an axis;

a variable conductance element between said high temperature interface and said low temperature interface and thermally connected thereto to provide a heat flow path;

means for thermally connecting a test sample to said high temperature interface;

means for heating said connected test sample;

a cryocooler having a cold head thermally connected to said low temperature interface, said test sample being coolable through said variable conductance element and said interfaces by operation of said cryocooler; and means for interacting said test sample with said evaluation unit, wherein said interfaces apply pressure respectively on said conductance element to improve thermal conduction, said pressure acting transversely to said axis.

22. A test instrument as in claim 21, wherein said variable conductance element is one of sapphire, silicon, and quartz.

23. A test instrument as in claim 21, wherein said evaluation unit is one of a gas chromatograph, DMA, and DSC.

24. A heating/cooling interface for operating in a wide temperature range including cryogenic temperatures, comprising:

a variable conductance element having a thermal conductivity that varies inversely with a change in temperature, and a first end and a second end, said ends being spaced apart along a longitudinal axis, when plotted on a graph with normalized integral $k\Delta T$ versus T coordinates between $T_c$ and $T_h$, said conductance element having a characteristic with a slope at $T_c$ that is greater and at $T_h$ a slope that is less than $1/(T_h-T_c)$, where $T_h$ is the high operating temperature and $T_c$ is the low operating temperature of said interface;

a first thermal interface element contacting said conductance element at said first end for heat transfer between said conductance element and said first thermal interface element, and for connecting to a cold head of a cryocooler system for heat transfer;

a second thermal interface element contacting said conductance element at said second end for heat transfer between said conductance element and said second thermal interface element, and for thermal connection to a test subject;

means for applying thermal energy to said second thermal interface element;

said test subject being subject to controllable heating and cooling when said interface is connected to said cold head and said means for applying thermal energy operates, wherein said interface elements apply pressure respectively on said conductance element to improve thermal conduction, said pressure acting transversely to said axis.

* * * * *